United States Patent
Rabinovich-Guilatt et al.

(10) Patent No.: US 9,132,071 B2
(45) Date of Patent: Sep. 15, 2015

(54) COMPOSITIONS CONTAINING QUATERNARY AMMONIUM COMPOUNDS

(75) Inventors: Laura Rabinovich-Guilatt, Kadima (IL); Gregory Lambert, Chatenay Malabry (FR); Frederic Lallemand, Fresnes (FR); Betty Philips, Antony (FR)

(73) Assignee: SANTEN SAS, Evry (FR)

( * ) Notice: Subject to any disclaimer, the term of this patent is extended or adjusted under 35 U.S.C. 154(b) by 1040 days.

(21) Appl. No.: 12/010,778

(22) Filed: Jan. 30, 2008

(65) Prior Publication Data

US 2008/0194532 A1    Aug. 14, 2008

Related U.S. Application Data

(63) Continuation-in-part of application No. 11/494,493, filed on Jul. 28, 2006, now abandoned.

(30) Foreign Application Priority Data

Jul. 28, 2006  (EP) .................................... 06291236

(51) Int. Cl.
| | |
|---|---|
| *A61F 2/00* | (2006.01) |
| *A61K 8/06* | (2006.01) |
| *A61K 8/41* | (2006.01) |
| *A61K 9/00* | (2006.01) |
| *A61Q 17/00* | (2006.01) |
| *A61Q 19/00* | (2006.01) |

(52) U.S. Cl.
CPC . *A61K 8/06* (2013.01); *A61K 8/062* (2013.01); *A61K 8/416* (2013.01); *A61K 9/0048* (2013.01); *A61Q 17/005* (2013.01); *A61Q 19/005* (2013.01)

(58) Field of Classification Search
CPC ... A61K 9/0048; A61K 38/19; A61K 9/1075; A61K 47/186; A61K 31/14; A61K 8/416; A61K 9/107; A61K 31/196; A61K 8/06; A61K 8/062; A61K 31/18; A61K 31/192; A61K 31/405; A61K 31/407; A61K 31/5415; A61K 31/60; A61K 2300/00; A61K 47/10; A61K 47/14; A61K 8/046; A61K 8/22; A61K 9/122; A61Q 17/005; A61Q 19/00; A61Q 19/005; A61Q 19/10; A61Q 1/14; A61Q 11/00
See application file for complete search history.

(56) References Cited

U.S. PATENT DOCUMENTS

| | | |
|---|---|---|
| 3,954,644 A | 5/1976 | Krezanoski et al. |
| 5,188,826 A | 2/1993 | Chandrasekaran et al. |
| 5,190,936 A | 3/1993 | Laugier et al. |
| 5,767,153 A | 6/1998 | Bowman et al. |
| 5,951,988 A | 9/1999 | Littel-van den Hurk et al. |
| 6,375,936 B1 | 4/2002 | Allard et al. |
| 6,635,676 B2 * | 10/2003 | Baker et al. ............... 514/642 |
| 2003/0165545 A1 * | 9/2003 | Huth et al. ................ 424/400 |
| 2005/0158349 A1 * | 7/2005 | Jampani et al. ........... 424/401 |
| 2006/0100288 A1 | 5/2006 | Bague et al. |
| 2007/0231406 A1 * | 10/2007 | Bucalo et al. ............. 424/617 |
| 2008/0279949 A1 * | 11/2008 | Merisko-Liversidge et al. ............... 424/489 |

FOREIGN PATENT DOCUMENTS

| | | |
|---|---|---|
| EP | 0642782 A2 | 3/1995 |
| GB | 633175 A | 12/1949 |
| WO | 9531958 A1 | 11/1995 |
| WO | 9725975 A1 | 7/1997 |

OTHER PUBLICATIONS

Adriaens et al., "The Mucosal Toxicity of Different Benzalkonium Chloride Analogues Evaluated with an Alternative Test Using Slugs", Pharmaceutical Research, vol. 18, No. 7, 2001.
Pignatello et al., "Flurbiprofen-loaded Acrylate Polymer Nanosuspensions for Ophthalmic Application", Biomaterials, 2002, vol. 23, pp. 3247-3255.

* cited by examiner

*Primary Examiner* — Lezah Roberts
*Assistant Examiner* — Nannette Holloman
(74) *Attorney, Agent, or Firm* — Young & Thompson (57) ABSTRACT

Compositions containing quaternary ammonium compounds in which the nitrogen atom is substituted by at least one alkyl group having at least 12 carbon atoms, where composition includes at least 20% in weight by weight of the total composition, of ammonium halides in which the nitrogen atom is substituted by at least one alkyl group having at least 14 carbon atoms and more than 5%, preferably more than 7% in weight by weight of the total composition, of ammonium halides in which the nitrogen atom is substituted by at least one alkyl group having at least 16 carbon atoms. Ophthalmic oil-in-water emulsions containing such compositions, and the ophthalmic emulsions being are useful for eye care or for the treatment of eye conditions.

19 Claims, 2 Drawing Sheets

COMPOSITIONS CONTAINING QUATERNARY AMMONIUM COMPOUNDS

This application is a continuation-in-part of application Ser. No. 11/494,493, filed Jul. 28, 2006, the entire contents of which is hereby incorporated by reference.

BACKGROUND OF THE INVENTION

1. Field of the Invention

This invention relates to pharmaceutical, ophthalmic or cosmetic compositions containing quaternary ammonium compounds, more preferably to ophthalmic emulsions being useful for eye care or for the treatment of eye conditions. This invention also relates to compositions including at least one quaternary ammonium compound as a cationic agent.

2. Description of the Related Art

Quaternary ammonium compounds are organic compounds usually used as antiseptic or antimicrobial agents. For example, benzalkonium chloride is a nitrogenous cationic surface-acting agent belonging to the quaternary ammonium group. Benzalkonium chloride is generally defined as a mixtures of compounds of general formula $C_6H_5CH_2N(CH_3)_2$ RCl, where R is a $C_{12}$-$C_{24}$ alkyl group.

Benzalkonium chloride, as usually provided by the manufacturers wanting to comply with the European and/or American Pharmacopeia, is a mixture of n-alkyl dimethyl benzyl ammonium chlorides of various alkyl chain lengths. For example, FeF Chemicals A/S (Denmark) supplies, under reference 8100301U (BAK USP/NF), a mixture of three alkyl dimethyl benzyl ammonium chlorides including: (1) 60-70% of $C_{12}$-alkyl dimethyl benzyl ammonium chloride (2) 30-40% of $C_{14}$-alkyl dimethyl benzyl ammonium chloride, and less than 5% of $C_{16}$-alkyl dimethyl benzyl ammonium chloride Benzalkonium chloride, as a mixture of alkyl dimethyl benzyl ammonium having various alkyl chain lengths is used as preservative agent in topical ophthalmic products. Benzalkonium chloride also has cationic agent properties, and was used as cationic agents for emulsions, especially ophthalmic emulsions.

When mixtures of benzalkonium chlorides having various alkyl chain lengths are used in emulsions, they may act both as preservative agents and cationic agents. However, the toxicity of these materials renders their use problematic.

SUMMARY OF THE INVENTION

The Applicant worked on long chain quaternary ammonium compounds, and noticed that the length of the alkyl chain was important with regards to the function performed by the quaternary ammonium compounds: acting on the length of the alkyl chain resulted in enhancing or reducing the cationic power of the quaternary ammonium compounds. Without wanting to be linked by any theory, the Applicant observed on working on oil-in-water emulsions, that long chain quaternary ammonium compounds are preferentially localized at the oil/water interface of the emulsions, resulting in (1) emulsions with higher zeta potential and (2) more stable emulsions. As quaternary ammonium may be considered as undesirable or toxic, it is thus a goal of this invention to provide cationic composition having a reduced content of quaternary ammonium compound.

The Applicant also observed that, in emulsions, quaternary ammonium compounds having long alkyl chains, for example quaternary ammonium compounds having $C_{14}$-$C_{18}$ alkyl chains, when compared to $C_{12}$-alkyl chains, did not have good bactericidal activity, whereas they conferred the greatest cationic power.

Moreover, the Applicant observed that long chain quaternary ammonium compounds were present preferentially at the oil/water interface of the emulsion droplets, and less in the aqueous phase. The fact that quaternary ammonium compounds may be present in the aqueous phase in a very small amount only, or not present, leads to a loss of preservative effect or poor preservative effect, as well as to less toxic emulsions.

Thus, one of the goals of this invention is to provide stable cationic emulsions comprising a reduced amount of benzalkonium chlorides, and still using the benzalkonium chlorides as a source, or the only source, of cationic agents, said emulsions being preserved or not.

Preferably, the emulsions of the invention are useful for cosmetic or ophthalmic purposes.

Another goal of this invention is to provide ammonium halide compositions, preferably benzalkonium compositions, suitable for the preparation of cationic emulsions. Preferably, said cationic emulsions are useful for ophthalmic or cosmetic purposes.

The invention, in part, pertains to an emulsion formed from water and a composition including at least one quaternary ammonium halide in which the nitrogen atom is substituted by at least one alkyl group having at least 12 carbon atoms, wherein the composition comprises about 20%-100%, preferably about 80%-100%, more preferably about 90%-100%, and even more preferably about 95%-100% by weight of the total composition, of quaternary ammonium halides in which a nitrogen atom is substituted by an alkyl group having at least 16 carbon atoms.

It is to be understood that both the foregoing general description and the following detailed description are exemplary and explanatory and are intended to provide further explanation of the invention as claimed.

BRIEF DESCRIPTION OF THE DRAWING FIGURES

The accompanying drawings are included to provide a further understanding of the invention. The drawings illustrate embodiments of the invention and together with the description serve to explain the principles of the embodiments of the invention.

DETAILED DESCRIPTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

This invention relates to a composition comprising at least one quaternary ammonium halide, more preferably ammonium chloride or bromide, in which the nitrogen atom of the ammonium group is substituted by at least one alkyl group having at least 12 carbon atoms, said composition including:

a) at least 20% in weight by weight of the total composition, of ammonium halides in which the nitrogen atom is substituted by at least one alkyl group having at least 14 carbon atoms, preferably 14 or 16 carbon atoms and b) more than about 5%, preferably more than about 7% in weight by weight of the total composition, of ammonium halides in which the nitrogen atom is substituted by at least one alkyl group having at least 16 carbon atoms.

According to an embodiment of the invention, the composition includes at least about 20% w/w of the total composition, of $C_{14}$-alkyl ammonium halides and at least 10%, preferably at least 15%, more preferably at least 20% w/w of the total composition, of $C_{16}$-alkyl ammonium halides.

According to another embodiment, the composition includes as only alkyl ammonium halide, $C_{16}$-alkyl ammonium halide, preferably $C_{16}$-alkylbenzyldimethyl ammonium halide. Preferably, the ammonium halides used in this invention are benzyl dimethyl ammonium chlorides or bromides, wherein the nitrogen atom is further substituted by an alkyl group having at least 12 carbon atoms, preferably 12, 14 and/or 16 carbon atoms.

According to an embodiment of the invention, the composition comprises $C_{14}$- and $C_{16}$-alkyl benzyl dimethyl ammonium chlorides. In a further embodiment, the composition of the invention does not include any $C_{12}$-alkyl ammonium halide.

According to another embodiment, the composition of the invention includes trimethyl ammonium chloride or bromide, wherein the nitrogen atom is further substituted by an alkyl group having at least 12 carbon atoms, preferably 12 and/or 14 and/or 16 carbon atoms. According to an embodiment, the trimethyl ammonium chloride or bromide is cetyltrimethyl ammonium bromide.

According to a further embodiment, and whatever the ammonium halides are, the amount of ammonium halides in which the nitrogen atom is substituted by at least one alkyl group having 14 or 16 carbon atoms may preferably represent at least about 50% w/w of the total amount of all ammonium halides present in the composition, this percentage being in dry weight.

According to another embodiment the amount of ammonium halides in which the nitrogen atom is substituted by at least one alkyl group having at least 16 carbon atoms may preferably represent more than 90% w/w measured in dry weight of the total amount of all ammonium halides present in the composition.

According to another embodiment the amount of ammonium halides in which the nitrogen atom is substituted by at least one alkyl group having at least 16 carbon atoms may preferably represent more than about 30% w/w measured in dry weight of the total amount of all ammonium halides present in the composition.

According to an embodiment of the invention, the composition includes, dry weight by total dry weight, of all ammonium halides present in the composition, 40% of ammonium halides in which the nitrogen atom is substituted by an alkyl group having 12 carbon atoms, 30% of ammonium halides in which the nitrogen atom is substituted by an alkyl group having 14 carbon atoms and 30% of ammonium halides in which the nitrogen atom is substituted by an alkyl group having 16 carbon atoms; preferably, the composition includes, measured in dry weight, in weight by total weight of all ammonium halides present in the composition, a mixture of about 40% w/w of BAK $C_{12}$, about 30% w/w of BAK $C_{14}$, and about 30% w/w of BAK $C_{16}$.

In another embodiment, the composition includes, in dry weight by total dry weight, a mixture of about 40% w/w ATAB $C_{12}$, about 30% w/w ATAB $C_{14}$ or about 30% w/w ATAB $C_{16}$.

In another embodiment, the mean molecular weight of the ammonium halides present in the composition is less than 372, this calculation based on the total alkyl basis.

In another embodiment, the composition consists of, in dry weight by total dry weight of the halide ammonium composition, about 85% of ammonium halides in which the nitrogen atom is substituted by an alkyl group having 14 carbon atoms and about 15% of ammonium halides in which the nitrogen atom is substituted by an alkyl group having 16 carbon atoms.

In another embodiment, the composition consists of about 45% of ammonium halides in which the nitrogen atom is substituted by an alkyl group having 12 carbon atoms and about 55% ammonium halides in which the nitrogen atom is substituted by an alkyl group having 16 carbon atoms.

According to an embodiment, the weight ratio of $C_{12}$-alkyl ammonium halides to the sum of $C_{14}$-alkyl ammonium halides and $C_{16}$-alkyl ammonium halide is less than about 1.5, preferably less than about 1.35, more preferably less than about 1.20. More preferably, the weight ratio of BAK $C_{12}$ to the sum of BAK $C_{14}$ and BAK $C_{16}$ is less than about 1.5, preferably less than about 1.35, more preferably less than about 1.20.

According to an embodiment of the invention, the composition includes more than one ammonium halide: in a first embodiment the composition includes three ammonium halides, preferably a $C_{12}$-alkyl ammonium halide and a $C_{14}$-alkyl ammonium halide and a $C_{16}$-alkyl ammonium halide, more preferably BAK $C_{12}$, BAK $C_{14}$ and BAK $C_{16}$. In another embodiment, the composition includes two ammonium halides, preferably a $C_{14}$-alkyl ammonium halide and a $C_{16}$-alkyl ammonium halide, preferably BAK $C_{12}$ and BAK $C_{16}$. In another embodiment of the invention, the composition includes only one ammonium halide, preferably $C_{16}$-alkyl ammonium halide, more preferably BAK $C_{16}$.

This composition is obtained by mixing various components obtained from commercial source, or by de novo synthesis of the composition itself, or by purification of commercial products.

In the meaning of this invention:

"cationic emulsions" are emulsions having a positive zeta potential, preferably a zeta potential higher to 10 mV;

"long alkyl chain" are alkyl moieties having at least 14 carbon atoms;

"quaternary ammonium compounds" refer to ammonium halides in which the nitrogen atom is substituted by at least one alkyl group having at least 12 carbon atoms; quaternary ammonium compounds also, but not exclusively, include n-alkyl dimethyl benzyl ammonium chloride also called benzalkonium chloride (hereafter also referred to as BAK or ADBAC); n-alkyl dimethyl benzyl ammonium bromide; n-alkyl trimethyl ammonium bromide (also referred to as ATAB), n-alkyl meaning an alkyl group of at least 12 carbon atoms;

"$C_{14}$-alkyl ammonium halides" means ammonium halides in which the nitrogen atom of the ammonium group is substituted by at least one alkyl group having at least 14 carbon atoms.

"BAK $C_{12}$" refers to benzododecinium chloride (CAS 139-07-1); "BAK $C_{14}$" refers to myristalkonium chloride (CAS 139-08-2); "BAK $C_{16}$" refers to cetylkonium chloride (CAS 122-18-9);

"ATAB $C_{12}$" refers to lauryl trimethyl ammonium bromide (CAS 1119-94-4); "ATAB C14" refers to Myristil trimethyl ammonium bromide (CAS 1119-97-7); "ATAB $C_{16}$" or "CTAB" refers to cetyl trimethyl ammonium bromide (CAS 57-09-0), "MCT" means medium chain triglycerides; for the experimentation, TCM™ (Societé des Oleagineux, France) was the MCT used; and "ND" means "not determined".

The invention also relates to a cationic oil-in-water emulsion comprising a composition of the invention, as described above. According to an embodiment of the invention, the oil-in-water emulsion comprises a composition as described above, the emulsion comprising about 0.0005 to 0.1% of quaternary ammonium halides. By cationic oil-in water emulsion is understood an oil-in-water emulsion having a positive zeta potential. The emulsion of the invention has a positive zeta potential and is stable, which means that it keeps a positive zeta potential overtime. In a preferred embodiment, the oil-in-water emulsion according to the invention includes droplets of a size of about 100 to 500 nm, preferably about 110 to 250 nm.

In a first embodiment, the oil-in-water emulsion of the invention is for cosmetic use. Preferably, the emulsion of the invention is intended for making up or caring for the body and face skin, including the lips, or for hair care. The cosmetic emulsion of the invention can be a product for caring for the skin, such as a care base for the skin, a care cream (e.g., day cream, night cream, anti-wrinkle cream), a make-up base or a composition for caring for the lips (e.g., lip balm), or make-up remover, including eye make-up remover. The product of the invention may also be used for enhancing moisture of hair and/or skin.

In a preferred embodiment, the oil-in-water emulsion of the invention is useful for eye care or for the treatment of eye diseases or eye conditions.

In the meaning of the invention, eye diseases or eye conditions means a wide variety of ocular conditions such as glaucoma, ocular inflammatory conditions such as keratitis, uveitis, intra-ocular inflammation, allergy and dry-eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation.

More preferably, the oil-in-water emulsion according to the invention comprises:

a) an oil phase, b) about 0.0005 to 0.1% w/w of a composition of quaternary ammonium halides, which contain at least 20% w/w, of ammonium halides in which the nitrogen atom is substituted by at least one alkyl group having at least 14 carbon atoms, preferably 14 or 16 carbon atoms and more than 5% w/w, preferably more than 7% w/w of ammonium halides in which the nitrogen atom is substituted by at least one alkyl group having at least 16 carbon atoms, in weight by weight of the total emulsion c) surfactants, d) optionally antioxidants, isotonicity, viscosifying, pH adjusting, buffering, preservative, solubilizers, chelating, thickener agents, and e) water.

According to an embodiment of the invention, the oil-in-water emulsion further comprises hydroxypropyl guar or polyethylene glycol-400 or a mixture of both.

According to an embodiment of the invention, the emulsion includes an oil phase, surfactants such as for example tyloxapol or poloxamer or tocopherol polyethyleneglycol succinate or polysorbate 80 or any suitable surfactant, and about 0.0005% to 0.1% w/w preferably about 0.001 to 0.005% w/w of the total composition, of a composition of ammonium halides according to the invention, as described above.

According to an embodiment of the invention, the emulsion includes $C_{12}$-alkyl benzyl dimethyl ammonium chloride or bromide, $C_{14}$-alkyl benzyl dimethyl ammonium chloride or bromide, and $C_{16}$-alkyl benzyl dimethyl ammonium chloride or bromide. According to another embodiment of the invention, the emulsion comprises $C_{14}$- and $C_{16}$-alkyl benzyl dimethyl ammonium chlorides. In a further embodiment, the emulsion of the invention does not include any $C_{12}$-alkyl ammonium chloride or bromide. According to an embodiment, the oil-in-water emulsion includes $C_{16}$-alkyl quaternary ammonium halide as only source of quaternary ammonium halide.

According to another embodiment, the emulsion of the invention includes trimethyl ammonium chlorides or bromides, wherein the nitrogen atom is further substituted by an alkyl group having at least 12 carbon atoms; or by an alkyl group having at least 14 carbon atoms; or by an alkyl group having at least 16 carbon atoms; or by a mixture of such trimethyl ammonium chlorides or bromides.

According to a preferred embodiment, the emulsion of the invention includes MCT, glycerol, tyloxapol and poloxamer, and a composition of the invention including at least one ammonium halide as described above.

Preferably, the emulsion includes about 1 to about 2% of oil phase, preferably of MCT, castor oil or mineral oil.

Preferably, the emulsion includes about 0.1 to about 1% of surfactants, preferably tyloxapol and/or poloxamer and/or polysorbate 80 and/or tocopherol polyethyleneglycol succinate.

In a preferred embodiment, the emulsion includes an oil phase, preferably about 2% MCT or about 1% mineral oil, and surfactants, preferably about 0.3% Tyloxapol and about 0.1% Poloxamer, optionally antioxidants such as alpha-tocopherol and optionally isotonicity agents such as mannitol or glycerol, and a composition of ammonium halides, preferably BAK $C_{12}$, BAK $C_{14}$, BAK $C_{16}$ or a mixture of at least two thereof, or in another embodiment ATAB $C_{12}$, ATAB $C_{14}$ or ATAB $C_{16}$ or a mixture of at least two thereof, said ammonium halides composition being in a concentration ranging from about 0.0005 to about 0.1% w/w of the total emulsion.

According to a first embodiment, the emulsion does not contain any active principle. In this embodiment, the emulsion is particularly useful as artificial tears, or for the treatment of dry eye condition such as for example Dry Eye Syndrome or Chronic Dry Eye Disease (CDED), both clinically known as keratoconjuctivitis sicca.

According to a second embodiment, the composition of the invention contains an active principle, preferably chosen among antibiotics such as aminoglycosides, carbacephem, carbapenems, cephalosporins, glycopeptides, penicillins, polypeptides, quinolones, sulfonamides, tetracyclines and others; antiviral agents such as cidofovir, ganciclovir, valaciclovir or acyclovir; antifungals such as polyene antibiotics, azole derivatives, imidazole, triazole and allylamines; intraocular pressure lowering agents such as alpha-adrenergic agonists, beta-adrenergic blockers, carbonic anhydrase inhibitors, cannabinoids, prostaglandins, prostaglandins analogues, derivatives and prodrugs; anti-inflammatory agents such as COX-2 inhibitors, salicylates, 2-arylpropionic acids, N-arylanthranilic acids, oxicams, sulphonanilides, pyrazolidines derivatives, arylalkanoic acids, 3-benzolphenylacetic acids and derivatives; steroids such as cortisone, hydrocortisone, prednisone, prednisolone, methylprednisone, fluorometethalone, medrysone, betamethasone, loteprednol, flumethasone, mometasone, testosterone, methyltestosterone, danazol, beclomethasone, dexamethasone, dexamethasone palmitate, triamcinolone, triamcinolone acetonide, fluocinolone, fluocinolone acetonide and difluprednate; antiallergic compounds such as olapatadine, ketotifen, azelastine, epinastine, emedastine, levocabastive, terfenadine, astemizole and loratadine; anti-angiogenic compounds such as thalidomide, VEGF inhibitors, VEGF soluble receptors, VEGF-traps, VEGF-antibodies, VEGF-traps, anti VEGF-siRNA; biological agents such as such as antibodies or antibodies fragments, oligoaptamers, aptamers and gene fragments, oligonucleotides, plasmids, ribozymes, small interference RNA, nucleic acid fragments, peptides and antisense sequences; growth factors such as epidermal growth factor, fibroblast growth factor, platelet derived growth factor, transforming growth factor beta, ciliary neurotrophic growth factor, glial derived neurotrophic factor, NGF, EPO and P1GF; immunomodulating agents such as glucocorticoids, drugs acting on immunophilins, interferons, opioids; cytostatics such as alkylating agents, antimetabolites and cytotoxic antibiotics; antioxidants such as alpha-tocopherol, ascorbic acid, retinoic acid, lutein and their derivatives, precursors or prodrugs; UV-filter compounds such as benzophenones; anti-redness agents such as naphazoline, tetrahydrozoline, ephedrine and phenylephrine; fatty acids such as omega-3 fatty acids.

Preferably, the composition of the invention contains an active principle chosen among the group consisting of ganciclovir, acyclovir, ketoconazole, amphotericin B, brimonidine, dexanabinol, forskolin, travoprost, latanoprost, amfenac, diclofenac, flurbiprofen, flurbiprofen axetyl, ketorolac, dexamethasone palmitate, rimexolone, triamcinolone, difluprednate, fluocinolone, olapatadine, alpha-tocopherol, vitamin A, vitamin C, lutein, eicosapentaenoic acid, docosahexaenoic acid, octylmethoxycinnamate, benzophenone-3, octyl dimethyl PABA, cyclosporine A, mycophenolate, sirolimus and tacrolimus and/or their derivatives; and/or their prodrugs; and/or their precursors; and/or acceptable salts thereof; alone or in combination.

In an embodiment, the emulsion of the invention includes cyclosporin A. In another embodiment, the invention includes cyclosporine A in combination with an azole derivative preferably chosen among voriconazole and econazole.

In an embodiment of the invention, the oil-in-water emulsion is preserved.

In another embodiment of the invention, the oil-in-water emulsion is unpreserved; in an embodiment, the emulsion is packaged in unitary doses. In another embodiment, the emulsion is packaged in suitable multidose containers.

The invention relates to a medicament comprising an oil-in-water emulsion as described above or a composition as described above.

The invention also relates to the use of an ophthalmic oil-in-water emulsion as described above or a composition as described above, especially for the manufacture of a medicament or an ophthalmic composition the treatment of an eye condition or disease.

The invention also relates to a cosmetic composition comprising an oil-in-water emulsion as described above or a composition as described above.

The invention also relates to a non-therapeutic process for caring for, removing makeup from and/or cleansing the skin, the lips and/or the eyes, and/or for hair care, comprising applying an oil-in-water emulsion as described above or a composition as described above to the skin, the lips, the eyes, and/or the hair.

The following examples and figures illustrate the invention and should not be interpreted in any way as reducing the scope of this invention.

EXAMPLES

All concentrations in the emulsion formulae are expressed in weight/weight of the entire formulation percentages, unless stated differently.

1. Emulsions Composition

Emulsions containing different amounts and chain lengths of BAK and ATAB were prepared. They contained 2% MCT or 1% mineral oil as oil phase, 0.3% Tyloxapol and 0.1% Poloxamer as surfactants. They could also contain antioxidants such as alpha-tocopherol and isotonicity agents such as mannitol or glycerol. Concentrations ranging from 0.001 to 0.1% of BAK C12, BAK C14, BAK C16 or a mixture of all, and from 0.0025 to 0.005% of ATAB C12, ATAB C14 or ATAB C16 were prepared.

2. Emulsions Preparation

The oily and the water phases of the emulsion, which might contain or not an active principle, may be separately heated to an appropriate temperature. This temperature may be the same in both cases. Surfactants might be dissolved in the oil, water phase or in both. A first coarse emulsion is generated by magnetic stirring, and the droplet size is reduced by high shear mixing, high pressure homogenization, or both.

The oil-in-water emulsions of the present invention can be sterilized after preparation using heat, for example, autoclave steam sterilization.

3. Impact of Chain Length on Emulsions Characteristics
a) Emulsion Droplet Size

The mean diameter of the oil droplets is determined by dynamic light scattering using a High Performance Particle Sizer type HPPS 5001 (Malvern Instruments, Worcestershire, UK). Measurements are performed at 25° C. following dilution of the emulsion in double distilled water. The emulsion droplet size values are shown in Table 1.

TABLE 1

| | Emulsion droplet size values (nm). | | | | | | |
|---|---|---|---|---|---|---|---|
| | 0.001% | 0.0025% | 0.005% | 0.01% | 0.02% | 0.04% | 0.1% |
| ATAB $C_{12}$ | — | — | — | — | — | — | — |
| ATAB $C_{14}$ | — | 203 | — | — | — | — | — |
| ATAB $C_{16}$ | — | 222 | 212 | — | — | — | — |
| BAK $C_{12}$ | — | — | 198 | 263 | 230 | 225 | 180 |
| BAK $C_{14}$ | — | 204 | 190 | 190 | 155 | 238 | 185 |
| BAK $C_{16}$ | 220 | 210 | 148 | 180 | 155 | 188 | 183 |
| 65% BAK $C_{12}$ 35% BAK $C_{14}$ | — | — | 357 | 397 | 190 | 180 | 156 |
| 40% BAK $C_{12}$ | — | 220 | 210 | 145 | — | — | — |

TABLE 1-continued

Emulsion droplet size values (nm).

| | 0.001% | 0.0025% | 0.005% | 0.01% | 0.02% | 0.04% | 0.1% |
|---|---|---|---|---|---|---|---|
| 30% BAK $C_{14}$ | | | | | | | |
| 30% BAK $C_{16}$ | | | | | | | | b) Emulsion Zeta Potential

Zeta potential can be measured by a zetameter such as Zetasizer 2000, Malvern Instruments Ltd, UK. The zeta potential of the emulsion droplet surface is determined by electrophoretic mobility. Measurements are performed at 25° C. following dilution at 1:250 of the emulsion in double distilled water. The electrophoretic mobility is converted into zeta potential values through the Smoluchowsky equation.

Figure 1:
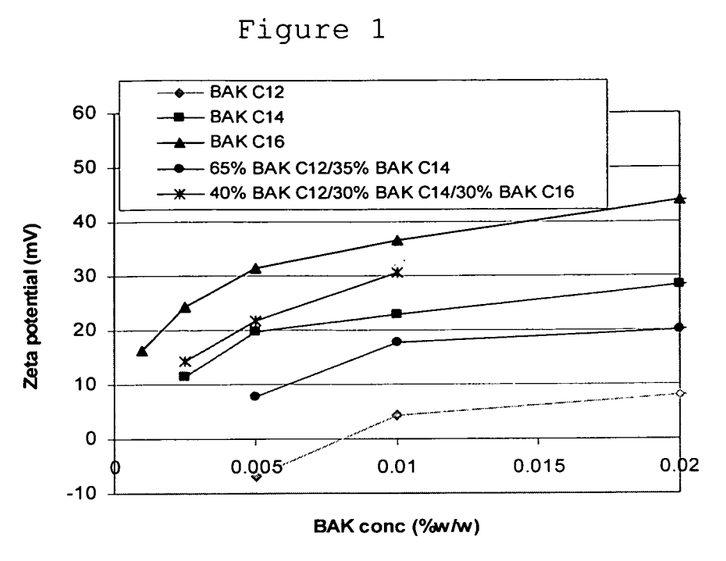
FIG. 1 is a graph showing zeta potential values (mV) of the emulsion of the invention depending of various BAK concentrations, and is to be read in connection with Table 2 of the examples.

The following table and graph show the evolution of the zeta potential (indicative of the surface charge) at increasing concentrations of QA. It can be observed that for more lipophilic (longer) chain lengths, positive charges are attained more rapidly and at lower concentrations, suggesting a preferential partition within the oil droplet surface. The emulsion zeta potential values are shown in Table 2.

TABLE 2

Emulsions zeta potential values (mV).

| | 0.001% | 0.0025% | 0.005% | 0.01% | 0.02% | 0.04% | 0.1% |
|---|---|---|---|---|---|---|---|
| ATAB $C_{12}$ | — | −35.5 | −14.6 | — | — | — | — |
| ATAB $C_{14}$ | — | −11.4 | −6.0 | — | — | — | — |
| ATAB $C_{16}$ | — | +11.9 | +20.2 | — | — | — | — |
| BAK $C_{12}$ | — | — | −6.9 | +4.2 | +7.9 | +16.8 | +23.8 |
| BAK $C_{14}$ | — | +11.4 | +19.6 | +22.9 | +28.4 | +39.3 | +44.5 |
| BAK $C_{16}$ | +16.2 | +24.4 | +31.4 | +36.7 | +44.1 | +47.2 | +48.9 |
| 65% BAK $C_{12}$ 35% BAK $C_{14}$ | — | — | +7.6 | +17.7 | +20.0 | +35.0 | +40.3 |
| 40% BAK $C_{12}$ 30% BAK $C_{14}$ 30% BAK $C_{16}$ | — | +14.3 | +21.6 | +30.7 | — | — | — |

FIG. 1 is a graph showing zeta potential values (mV) of the emulsion of the invention depending of various BAK concentrations.

3. Emulsion Stability Over Time

The stability of the emulsions can be evaluated by the evolution of their aspect, with a visual score with a visual score going from 13—best aspect to 1—total phase separation.

It can be observed from the following Table 3 that, at equimolar concentration, longer (more lipophilic) chain length QA results in more stable emulsion.

TABLE 3

Emulsion stability.

| Emulsion | Type and conc. of QA | After preparation (T0) | Following 3 months at 40° C. |
|---|---|---|---|
| Z01EM207 | 0.25 mM BAK $C_{12}$ | 12 | 2 |
| Z01EM208 | 0.25 mM BAK $C_{14}$ | 13 | 7 |
| Z01EM209 | 0.25 mM BAK $C_{16}$ | 13 | 9 |
| Z01EM204 | 0.5 mM BAK $C_{12}$ | 10 | 2 |
| Z01EM205 | 0.5 mM BAK $C_{14}$ | 13 | 7 |
| Z01EM206 | 0.5 mM BAK $C_{16}$ | 11 | 9 |

4. Impact of Chain Length on Antimicrobial Activity of QA

The antimicrobial effectiveness of the emulsions and solutions of BAK $C_{12}$, BAK $C_{14}$ and BAK $C_{16}$ at equimolar concentrations corresponding to 0.005% w/w BAK $C_{12}$ has been determined according to the chapter 51 of the United States Pharmacopeia. The results are shown in Table 4.

TABLE 4

Antimicrobial effectiveness testing of emulsions and solutions containing BAK $C_{12}$, $C_{14}$ or $C_{16}$.

| Chain length | BAK $C_{12}$ | BAK $C_{14}$ | BAK $C_{16}$ |
|---|---|---|---|
| Solution | ✓ (SOL226) | NA | ✓ (SOL254) |
| Emulsion | ✓ (EM212) | ✓ (EM219) | x (EM234) |

✓: preserved,
x: not preserved,
NA: not assessed

5. Impact of Chain Length on Toxicity of QA

The ocular irritation of the emulsions and solutions has been evaluated using an adaptation of the Draize test on white male New Zealand rabbits (2.75-3.00 kg). Fifty µL of emulsion or solution were instilled unilaterally and 50 µL of NaCl 0.9% in the other eye of the three rabbits per group. General aspect assessment of the animals was performed (behavior, blinking, itching of the eye with forelegs) as well as eye tissue evaluation (conjunctiva, cornea, iris) after instillation, 1, 24, 48 and 72 hours. Observations were scored according to the Draize test protocol.

Figure 2:
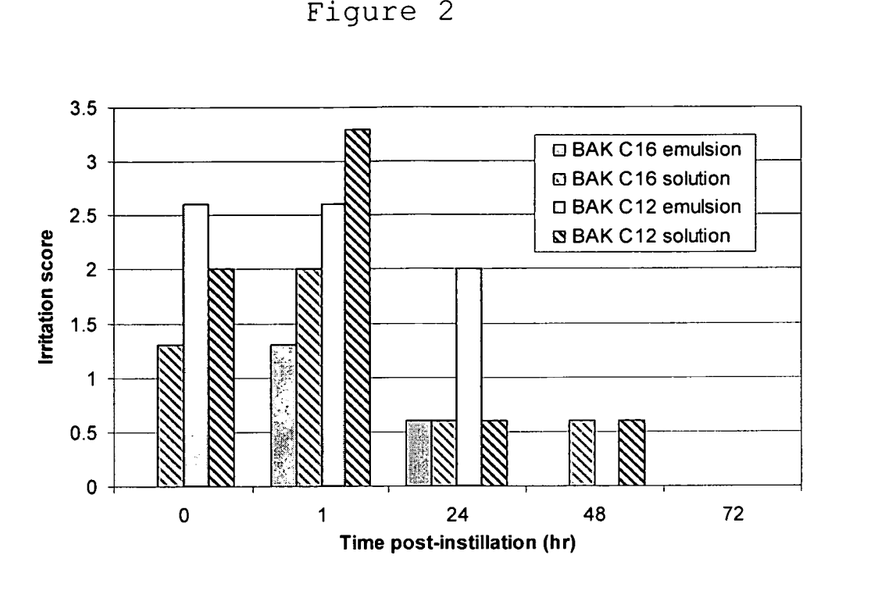
FIG. 2 is a graph showing the unexpected decrease of the toxicity of the emulsion comprising BAK $C_{16}$.

The graph (FIG. 2) shows that the incorporation of BAK $C_{16}$ within an emulsion results in an unexpected decrease of its toxicity.

6. Emulsions Containing Therapeutically Active Compound

Emulsions loaded with a therapeutically active compound (0.05% w/w Cyclosporin A) and containing different amounts and chain lengths of BAK were prepared as described previously. The resulting zeta potentials are shown in Table 5.

TABLE 5

Zeta potentials of active compound containing emulsions.

|  | w/w | Emulsion | Zeta potential (mV) |
|---|---|---|---|
| BAK $C_{16}$ | 0.002% | EM067 | +23.0 |
|  | 0.0025% | EM063 | +23.2 |
|  | 0.003% | EM070 | +26.7 |
|  | 0.005% | EM064 | +29.2 |
| 40% BAK $C_{12}$ | 0.005% | EM065 | +19.6 |
| 30% BAK $C_{14}$ | 0.01% | EM066 | +27.9 |
| 30% BAK $C_{16}$ |  |  |  |

In an additional embodiment of the present invention, an oil-in-water emulsion includes a composition formed from at least one quaternary ammonium halide in which the nitrogen atom is substituted by at least one alkyl group having at least 12 carbon atoms, where the composition can include about 20%-100%, preferably at least about 80%-100%, more preferably about 90%-100%, even more preferably about 95-100% in weight by weight of the total composition, of quaternary ammonium halides in which the nitrogen atom is substituted by one alkyl group having at least 16 carbon atoms, preferably having 16 carbon atoms, preferably being cetalkonium chloride (CKC).

This oil-in-water emulsion can include about 0.0005 to about 0.1%, preferably about 0.002% to about 0.01% of said composition. The balance may include up to about 99.9995 to about 99.9% water. Other materials may be present in the emulsion.

According to a preferred embodiment, the oil-in-water emulsion includes a composition formed from more than about 95% of CKC.

The oily phase of the emulsion may include: triglycerides such as medium chain triglycerides (MCT) or long chain triglycerides, or modified propylene glycol such as propylene glycol diesters; mineral oils such as heavy or light mineral oil; vegetable oils such as castor oil, olive oil, corn oil, soya oil, peanut oil, cottonseed oil, coconut oil, palm oil, almond oil, sesame oil. MCT is preferred.

The emulsion may include one or more surfactants, such as, for example, lecithins, sodium docusate, sodium lauryl sulphate, poloxamers, polyoxyethylene sorbitan fatty acids (polysorbates), polyoxyethylene castor oils derivatives (cremophors), tyloxapol, polyoxyethylene alkyl ethers (BRIJS).

The emulsion may include one or more osmotic agents.

In an embodiment of the present invention, the emulsion may include one or more additional cationic agents.

In another embodiment, the ammonium halide composition may be the only cationic agent that is included in the oil-in-water emulsion.

In further exemplary embodiments of the present invention, the following materials may be used:

Riluzole—Riluzole acts as a potent neuroprotective agent against pressure-induced ischemia. Therefore, riluzole may be a major drug for use in protection against retinal injury. (Invest Opthalmol V is Set. 1999; 40:729-736) Not on the ophthalmic market.

Fusidic acid—Fusidic acid is a bacteriostatic antibiotic that is often used topically in creams and eyedrops. Already used as Fucithalmic but there is a need to enhanced bioavailability.

Loratadine—Loratadine is a drug used to treat allergies (anti H1), and marketed for its nonsedating properties. Selected for its lipophilicity and the high potential market. Loratadine is not used in ophthalmology.

Tacrolimus—Tacrolimus is an immunosuppressive drug and a highly potent anti-inflammatory drug.

Naphazoline—Naphazoline is a vasoconstrictor used to avoid the redness of the conjunctivae. There are already two specialties on the market (Naphcon solution at 0.012% from Alcon; Vasoclear solution at 0.02% from Novartis). However, it is possible to combine this molecule with Cationorm to develop a new product.

Ketanserine—Ketanserine is a 5 HT2 antagonist potentially applicable in the treatment of glaucoma. It is usually used as a vasodilatator and hypertensive.

The following examples utilize these types of materials. Percentages are in % w/w.

Example A1

|  | Content in % w/w |
|---|---|
| Active substance |  |
| Riluzole | 0.50 |
| Excipients |  |
| MCT | 2.00 |
| Tyloxapol | 0.30 |
| CKC | 0.005 |
| Poloxamer 188 | 0.10 |
| Glycerol | 2.25 |
| Water | QS 100 |

Example A1 includes about 0.50% Riluzole active substance, about 2.00% MCT, about 0.30% Tyloxapol, about 0.005% CKC, about 0.10% Poloxamer 188, about 2.25% Glycerol, the balance being water.

Example A2

|  | Content in % w/w |
|---|---|
| Active substance |  |
| Riluzole | 0.40 |
| Excipients |  |
| Castor oil | 2.00 |
| CKC | 0.005 |
| Polysorbate 80 | 0.10 |
| Glycerol | 2.25 |
| Water | QS 100 |

Example A2 includes about 0.40% Riluzole active substance, about 2.00% Castor oil, about 0.005% CKC, about 0.10% Polysorbate 80, about 2.25% Glycerol, the balance being water.

Example A3

|  | Content in % w/w |
|---|---|
| Active substance | |
| Fusidic acid | 0.20 |
| Excipients | |
| MCT | 2.00 |
| Propylene glycol | 2.00 |
| Tyloxapol | 0.30 |
| CKC | 0.005 |
| Poloxamer 188 | 0.10 |
| Water | QS 100 |

Example A3 includes about 0.20% Fusidic acid active substance, about 2.00% MCT, about 2.00% propylene glycol, about 0.30% Tyloxapol, about 0.005% CKC, about 0.10% Poloxamer 188, the balance being water.

Example A4

|  | Content in % w/w | |
|---|---|---|
| Active substance | | |
| Latanoprost | 0.004 | 0.005 |
| Excipients | | |
| Olive oil | 1.000 | 1.000 |
| CKC | 0.005 | 0.005 |
| Glycerol | 2.400 | 2.400 |
| Polysorbate 80 | 0.050 | 0.050 |
| Water | qs 100 | qs 100 |

Example A4 includes about 0.004% or about 0.005% Latanoprost active substance, about 1.00% olive oil, about 0.005% CKC, about 2.400% glycerol, about 0.050% Polysorbate 80, the balance being water.

Example A5

|  | Content in % w/w |
|---|---|
| Active substance | |
| Loratadine | 0.08 |
| Excipients | |
| MCT | 2.00 |
| Propylene glycol | 2.00 |
| Tyloxapol | 0.30 |
| CKC | 0.005 |
| Poloxamer 188 | 0.10 |
| Water | QS 100 |

Example A5 includes about 0.08% Loratadine active substance, about 2.00% MCT, about 2.00% propylene glycol, about 0.30% Tyloxapol, about 0.005% CKC, about 0.10% Poloxamer 188, the balance being water.

Example A6

|  | Content in % w/w |
|---|---|
| Active substance | |
| Tacrolimus | 0.10 |
| Excipients | |
| MCT | 2.00 |
| PEG 400 | 2.00 |
| Tyloxapol | 0.30 |
| CKC | 0.005 |
| Glycerol | 1.90 |
| Poloxamer 188 | 0.10 |
| Water | QS 100 |

Example A6 includes about 0.10% Tacrolimus active substance, about 2.00% MCT, about 2.00% PEG 400, about 0.30% Tyloxapol, about 0.005% CKC, about 1.90% glycerol, about 0.10% Poloxamer 188, the balance being water.

Example A7

|  | Content in % w/w |
|---|---|
| Active substance | |
| Naphazoline | 0.03 |
| Excipients | |
| Heavy mineral oil | 0.50 |
| Light mineral oil | 0.50 |
| Tyloxapol | 0.30 |
| CKC | 0.005 |
| Glycerol | 2.25 |
| Poloxamer 188 | 0.10 |
| Water | QS 100 |

Example A7 includes about 0.03% Naphazoline active substance, about 0.50% heavy mineral oil, about 0.50% light mineral oil, about 0.30% Tyloxapol, about 0.005% CKC, about 2.25% glycerol, about 0.10% Poloxamer 188, the balance being water.

Example A8

|  | Content in % w/w |
|---|---|
| Active substance | |
| Ketanserine | 0.01 |
| Excipients | |
| Olive oil | 1 |
| CKC | 0.005 |
| Cremophor RH40 | 0.50 |
| Glycerol | 2.25 |
| Poloxamer 188 | 0.10 |
| Water | QS 100 |

Example A8 includes about 0.01% Ketanserine active substance, about 1% olive oil, about 0.005% CKC, about 0.50%

Cremophore RH40, about 2.25% glycerol, about 0.10% Poloxamer 188, the balance being water.

Example A9

|  | Content in % w/w |
| --- | --- |
| Oily Phase | |
| MCT | 5 |
| Polysorbate 80 | 1 |
| Voriconazole | 0.2 |
| Cyclosporine A | 0.05 |
| Aqueous Phase | |
| CKC | 0.005 |
| Poloxamer 188 | 0.10 |
| Glycerol | 2.25 |
| Water | QS 100 |

Example A10

|  | Content in % w/w |
| --- | --- |
| Oily Phase | |
| MCT | 2 |
| Castor oil | 2 |
| Tyloxapol | 0.3 |
| Econazole | 0.5 |
| Cyclosporine A | 0.05 |
| Aqueous Phase | |
| CKC | 0.005 |
| Poloxamer 188 | 0.10 |
| Glycerol | 2.25 |
| NaOH 0.1N | QS pH 7 |
| Water | QS 100 |

Examples A9 and A10 are combinations of an azole compound with Cyclosporin A, which gives a synergic action for treatment of ophthalmic fungal infections such as fusariums.

The formulations of Examples A1-A10 exhibited good stability and effectiveness.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. An emulsion, comprising:
an aqueous phase comprising water; and
0.0005% to 0.1% by weight of the total emulsion of at least one alkyl (C12-C16) dimethyl- or trimethyl-benzyl ammonium halide, wherein at least 20% by weight of the ammonium halide is a C16-alkyl dimethyl- or trimethyl-benzyl ammonium halide
and wherein the emulsion droplets have a zeta potential of at least +14.3 mV, and the emulsion remains stable for at least three months after emulsification.

2. The emulsion according to claim 1, wherein the emulsion is an oil-in-water emulsion.

3. The emulsion according to claim 1, wherein at least 80% by weight of the ammonium halide is a C16-alkyl dimethyl- or trimethyl-benzyl ammonium halide.

4. The emulsion according to claim 1, wherein about 90% by weight of the ammonium halide is a C16-alkyl dimethyl- or trimethyl-benzyl ammonium halide.

5. The emulsion according to claim 1, wherein about 95% by weight of the ammonium halide is a C16-alkyl dimethyl- or trimethyl-benzyl ammonium halide.

6. The emulsion according to claim 1, wherein the alkyl (C12-C16) dimethyl- or trimethyl-benzyl ammonium halide is cetalkonium chloride.

7. The emulsion according to claim 1, comprising about 0.002% to about 0.01% by weight of the at least one alkyl (C12-C16) dimethyl- or trimethyl-benzyl ammonium halide.

8. The emulsion according to claim 1, wherein the emulsion includes an oily phase comprising at least one compound selected from the group consisting of triglycerides, medium chain triglycerides, long chain triglycerides, modified propylene glycol, propylene glycol diester, mineral oil, heavy mineral oil, light mineral oil, vegetable oil, castor oil, olive oil, corn oil, soya oil, peanut oil, cottonseed oil, coconut oil, palm oil, almond oil, and sesame oil.

9. The emulsion according to claim 1, wherein the emulsion includes an oily phase comprising medium chain triglycerides.

10. The emulsion according to claim 1, wherein the emulsion comprises at least one surfactant selected from the group consisting of lecithins, sodium docusate, sodium lauryl sulphate, poloxamers, polyoxyethylene sorbitan fatty acids, polyoxyethylene castor oils derivatives, tyloxapol, and polyoxyethylene alkyl ethers.

11. The emulsion according to claim 1, wherein the emulsion comprises at least one osmotic agent.

12. The emulsion according to claim 1, wherein the emulsion further comprises at least one additional cationic agent.

13. The emulsion according to claim 1, wherein the alkyl (C12-C16) dimethyl- or trimethyl-benzyl ammonium halide is the only cationic agent that is included in the emulsion.

14. The emulsion according to claim 1, wherein the emulsion further comprises an active substance selected from the group consisting of riluzole, fusidic acid, latanoprost, loratadine, tacrolimus, naphazoline and ketanserine.

15. An ophthalmic oil-in-water emulsion, comprising:
an aqueous phase comprising water;
0.0005% to 0.1% by weight of the total emulsion of at least one alkyl (C12-C16) dimethyl- or trimethyl-benzyl ammonium halide, wherein at least 20 by weight of the ammonium halide is a C16-alkyl dimethyl- or trimethyl-benzyl ammonium halide;
an oily phase; and
a surfactant,
and wherein emulsion droplets have a zeta potential of at least +14.3 mV, and the emulsion remains stable for at least three months after emulsification.

16. The emulsion according to claim 15, wherein at least 80% by weight of the ammonium halide is a C16-alkyl dimethyl- or trimethyl-benzyl ammonium halide.

17. The emulsion according to claim 15, wherein the alkyl (C12-C16) dimethyl- or trimethyl-benzyl ammonium halide is cetalkonium chloride.

18. The emulsion according to claim 15, wherein the oily phase comprises at least one compound selected from the group consisting of triglycerides, medium chain triglycerides, long chain triglycerides, modified propylene glycol, propylene glycol diester, mineral oil, heavy mineral oil, light mineral oil, vegetable oil, castor oil, olive oil, corn oil, soya oil, peanut oil, cottonseed oil, coconut oil, palm oil, almond oil, and sesame oil.

19. The emulsion according to claim 15, wherein the aqueous phase comprises at least 99.9% water.

* * * * *